United States Patent
Rodriguez et al.

(10) Patent No.: US 8,165,697 B2
(45) Date of Patent: Apr. 24, 2012

(54) ELECTRODE-BEARING GUIDE AND COCHLEAR IMPLANT

(75) Inventors: Manuel Manrique Rodriguez, Pamplona-Navarra (ES); Francisco Javier Gracia Gaudo, Pamplona-Navarra (ES)

(73) Assignee: Instituto Cientifico y Tecnologico de Navarra, S.A., Pamplona (ES)

( * ) Notice: Subject to any disclaimer, the term of this patent is extended or adjusted under 35 U.S.C. 154(b) by 995 days.

(21) Appl. No.: 10/539,520

(22) PCT Filed: Dec. 15, 2003

(86) PCT No.: PCT/ES03/00632
§ 371 (c)(1),
(2), (4) Date: Dec. 13, 2007

(87) PCT Pub. No.: WO2004/054474
PCT Pub. Date: Jul. 1, 2004

(65) Prior Publication Data
US 2008/0140156 A1    Jun. 12, 2008

(30) Foreign Application Priority Data
Dec. 18, 2002 (ES) .................................. 200202912

(51) Int. Cl.
*A61N 1/05* (2006.01)
(52) U.S. Cl. ..................................................... 607/137
(58) Field of Classification Search .................. 607/137
See application file for complete search history.

(56) References Cited

U.S. PATENT DOCUMENTS

| | | | |
|---|---|---|---|
| 5,720,099 A * | 2/1998 | Parker et al. ..................... | 29/825 |
| 6,374,143 B1 * | 4/2002 | Berrang et al. ............... | 607/137 |
| 6,408,496 B1 * | 6/2002 | Maynard ..................... | 29/25.35 |
| 6,643,552 B2 * | 11/2003 | Edell et al. ..................... | 607/116 |
| 7,813,796 B2 * | 10/2010 | Greenberg et al. ............... | 607/2 |
| 2003/0233134 A1 * | 12/2003 | Greenberg et al. .............. | 607/36 |
| 2004/0147825 A1 * | 7/2004 | Milojevic et al. .............. | 600/372 |

FOREIGN PATENT DOCUMENTS

| | | |
|---|---|---|
| JP | 07169649 | 7/1995 |
| JP | 10232215 | 9/1998 |
| JP | 11016488 | 1/1999 |
| JP | 2001310334 | 11/2001 |
| JP | 2002148809 | 5/2002 |
| WO | WO 96/31087 | 10/1996 |
| WO | WO 02/43623 | 6/2002 |
| WO | WO 02/080817 | 10/2002 |
| WO | WO 02/089907 | 11/2002 |
| WO | WO 03/041092 | 5/2003 |
| WO | WO 03/043529 | 5/2003 |
| WO | WO 03/090848 | 11/2003 |

* cited by examiner

*Primary Examiner* — Kennedy Schaetzle
(74) *Attorney, Agent, or Firm* — Kramer & Amado, P.C.

(57) ABSTRACT

The invention relates to an electrode-bearing guide, a cochlear implant comprising said guide and the production method thereof. According to the invention, the long and essentially flat guide comprises a plurality of electrodes (2) which are connected to corresponding contacts (3) by means of tracks (4). The inventive guide also comprises at least two stacked basic cells (CB1, CB2, . . . CB11), each of said cells comprising an insulating base layer (11). Moreover, a conductive layer (12) is disposed on top of the aforementioned insulating layer and forms the electrodes (2), the tracks (4) and the contacts (3). The production method consists in successively stacking insulating and conductive layers and defining suitable shapes by means of photolithography in order to form electrodes, contacts, tracks and windows for accessing the electrodes and contacts. The invention enables the automated production of a guide with a large number of electrodes, which is suitably dimensioned for the atraumatic implantation thereof outside the tympanic canal.

20 Claims, 4 Drawing Sheets

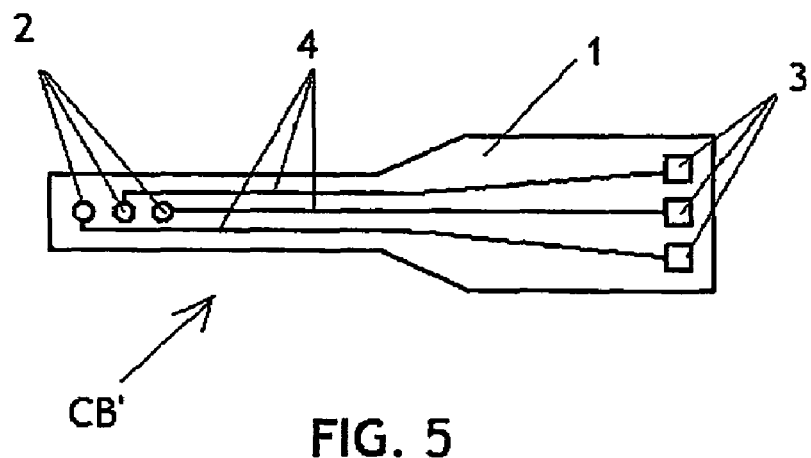
FIG. 5
FIG. 6
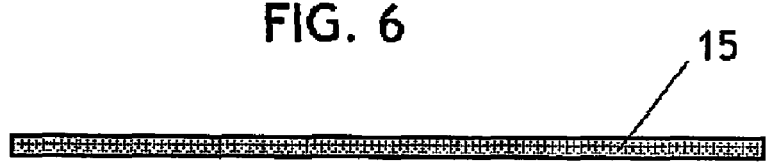
FIG. 7
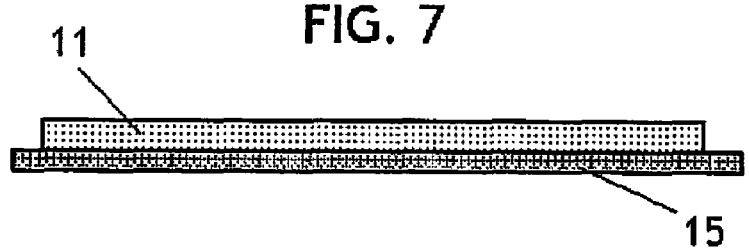
FIG. 8
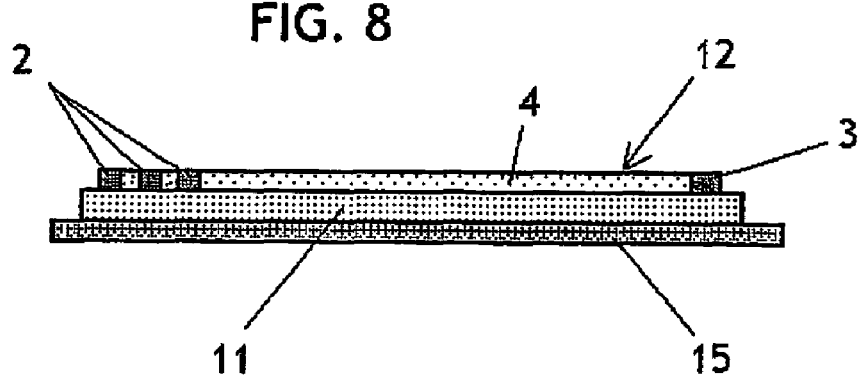

ELECTRODE-BEARING GUIDE AND COCHLEAR IMPLANT

The present invention relates to an electrode carrier guide, specially designed for cochlear implants, with a long, substantially flat shape, presenting a plurality of electrodes, each of them connected to the corresponding contact through a track.

The invention also relates to a cochlear implant and to a production method for electrode carrier guides.

BACKGROUND OF THE INVENTION

At this state of technology, several types of cochlear implants are known. These implants are conceived to improve the hearing of patients whose cochlea is not able to transform acoustic signals in nerve impulses.

Basically, a cochlear implant is a transducer that transforms acoustic signals in electric signals, applied to the hearing neural tissue by means of electrodes.

Cochlear implants usually include a round-shaped electrode carrier guide, with a series of electrodes lined up along it. The carrier guide is implanted in the scala tympani so that electrodes may remain close to the modiolus of the cochlea.

Patients treated with cochlear implants have extensively benefited from them. However, the conventional electrode carrier guides described above present some limitations.

First of all, its intracochlear insertion may result into damage the cochlea, by jeopardizing its anatomy and its function. We must not forget that the patients needing these systems are, for example, 2-year-old kids, with a life expectancy of 100 years, so the use of an atraumatic system is needed. Therefore, the potential use of other therapeutic treatments is not limited, and it enables to preserve residual hearing. This would permit to extend the indication of implants to people with a sensorineural hearing loss less severe than currently.

Another limitation to the traditional electrode carrier guides is that they only host up to 22 active electrodes, which limits the possibility to reproduce a more acute, punctual and versatile stimulation of the hearing neural tissue.

Besides, conventional carrier guides are hand-made by highly qualified and experimented staff. For obvious reasons, the production system is slow and expensive, plus it is highly probable that the resulting carrier guides contain a relatively high number of failures.

It has been recently proposed—for example in the patent application WO 02/080817—a cochlear implant with a flat electrode carrier guide, meant to be implanted externally to the scala tympani, exactly between the spiral ligament and the endosteum.

An implant such as the one described in this document has an advantageous feature regarding the traditional intraluminar implants: it may be inserted without damaging the morphology and function of the hearing neural tissue. However, even though this document recommends a maximum size for the electrode carrier guide, it does not suggest that the carrier guide may have a different structure from the one that conventional carrier guides have, or that it may not be automatically produced.

DESCRIPTION OF THE INVENTION

The main goal of the present invention is to provide a more efficiently produced electrode carrier guide, capable of hosting an elevated number of electrodes.

According to this goal, the invention presents an electrode carrier guide for cochlear implants comprising at least two stacked basic cells, each of the cells comprising an electricity-insulating base layer. An electricity-conducting layer is disposed on top of these layers and forms the electrodes, the tracks and the contacts.

These characteristics make the tracks connecting electrodes to their contacts remain isolated from each other and allow to place a higher number of tracks, and thus of electrodes, on a given carrier guide length. Furthermore, the carrier guide may be produced automatically, using miniaturization techniques to increase the number of electrodes and to reduce the influence of an electrode on its adjacents' signal.

The increase in the number of electrodes is an important factor, since it enables the implementation of new codification strategies, the adaptation of the stimulation to the state of the neural population of the cochlea, a more acute and punctual stimulation, a reduction of the refractory periods; in short, it provides us with a more versatile implantable system.

Furthermore, this electrode carrier guide may be given the adequate size to be implanted between the spiral ligament and the endosteum by means of an atraumatic surgery. Therefore, it may also be used for patients with a less severe sensorineural hearing loss, which increases the field of application of cochlear implants and enables its use in hybrid systems of bimodal stimulation, for instance those comprising a hearing aid and a cochlear implant or a middle ear implant and a cochlear implant. For this reason it may also be implanted in very young patients while preserving the possibility to use more powerful, sophisticated implants in the future. Another brand-new alternative offered by this design of flat electrode carrier guide, is to use it for conventional cases of profound hearing loss with little residual hearing, by placing it on an intraluminar level in the scala tympani of the cochlea.

In an advantageous embodiment, each basic cell is shorter than the underlying basic cell; and preferably, each basic cell covers the underlying cell except for the electrode area, in one end, and the contact area, in the other end.

Therefore, electrodes and contacts of each of the cells remain exposed without any other operation.

In some embodiments, each basic cell comprises an insulating layer placed on the electricity-conductive layer. The insulating layer presents access openings. Each of these corresponds with an electrode and a contact. The insulating layer avoids any possible interference between non-corresponding electrodes, tracks and contacts.

The insulating layer of each cell constitutes preferably the base layer of the superposed cell, so that a sole layer fulfils both functions and the total thickness is reduced.

The number of electrodes depends on the application and geometric dimensions of the carrier guide. In one embodiment, at least some of the basic cells present three electrodes, essentially aligned along the cell. The shape of the electrodes may vary depending on the application needs, being specially recommended the following shapes: rounded, squared, rectangular or oblong. The area of electrodes will depend on the level of current density required by the application as long as it is compatible with the limitations imposed by the total size of the carrier guide, and with the area reserved for the contacts and interconnections which in this embodiment are drawn in the same figures.

For some forecasted embodiments, the basic cells are between 0.3 mm and 2.5 mm wide; the base layer of each basic cell being between 2 μm and 5 μm thick, and the electricity-conductive layer being between 0.1 μm and 0.5 μm thick; and the distance between the electrodes of a basic cell being between 0.25 μm and 10 μm long.

According to a specially suitable embodiment from a biomedical point of view, the basic cells are narrower, at least on the side along which electrodes are placed. The form of this cell may be described as lancet-shaped.

According to some embodiments, the base layer material is selected among PTFE, PET, polyimide, silicone and polymers made of paraxylene; and the electricity conductive layer is made of a material selected among gold, platinum or an alloy of platinum and iridium.

Preferably each cell comprises a thin layer of a biodegradable material for a better adhesion. This layer should be between the base layer and the electricity-conductive layer. This way, a detachment of electrodes, contacts and tracks from the base layer is avoided. The adhesive material of the thin layer must be selected according to the biocompatibility criteria the application requires.

According to a second aspect, the present invention relates to a cochlear implant comprising an electrode carrier guide like the one described.

According to a third aspect, the present invention relates to a method for manufacturing electrode carrier guides, characterized in that it comprises a first step of forming one basic cell of at least one guide, having the following sub-steps:

(a) preparing a sacrificial wafer;
(b) depositing on said wafer a base layer made of an electrically insulating material;
(c) depositing on said electrically insulating layer a layer of photosensitive resin and photolithographically designing a geometry of electrodes, tracks and contacts;
(d) depositing on said resin layer a layer made of an electrically conducting material and then removing the resin and the electrically conducting material deposited outside the region of the photolithographically designed geometry;
(e) depositing a second electrically insulating layer, completely covering said electrically conducting layer; and
(f) forming on said second electrically insulating layer some accesses to the underlying electrodes and contacts, by opening access windows by means of photolithographic techniques and carrying out a chemical attack; and in that the sub-steps (c) to (f) are repeated on as much times as basic cells are intended to be piled up on each guide, and in that finally said sacrificial wafer is removed.

This method for manufacturing carrier guides permits an automated and parallel production of the guides. Therefore, it is low-cost. The possibility of a high degree of miniaturization allows increasing the number of electrodes, with the previously mentioned advantages.

Preferably at least two electrode carrier guides are formed on the wafer, said method further comprising a step of separating said guides from each other by cutting the wafer.

This way, several carrier guides may be produced simultaneously with the same structure, on a sole wafer.

In one embodiment at least two electrode carrier guides are formed on the wafer, and wherein in said sub-step (f) are also designed access windows opened for removing the electrically insulating material being between every two adjacent guides, in order to define the form of said guides and to have them separated from each other on the wafer.

This system enables you to produce carrier guides of any shape, for example lancet-shaped. To separate them by cutting through the wafer becomes unnecessary.

Advantageously, at least some of the sub-phases (b), (c), (e) and (f) comprise processes for curing the material.

According to some convenient embodiments, said sub-step (d) comprises depositing a film of a material enhancing adherence between said resin layer and said electrically conducting layer.

BRIEF DESCRIPTION OF THE DRAWINGS

In order to provide a better understanding of what has been exposed, you will find in the next pages some drawings representing a practical case of an embodiment. Please do bear in mind that they are schematic and a mere example, not a limitation.

Figures:

FIG. 5 is a top view of an alternative embodiment of a basic cell; and

FIGS. 6 to 11 are front views showing a production method of an electrode carrier guide, according to the embodiment of the invention.

DESCRIPTION OF THE PREFERRED EMBODIMENTS

An electrode carrier guide according to the present invention is formed by the superposition of a series of basic cells, each of them presenting at least one electrode.

Figure 1:
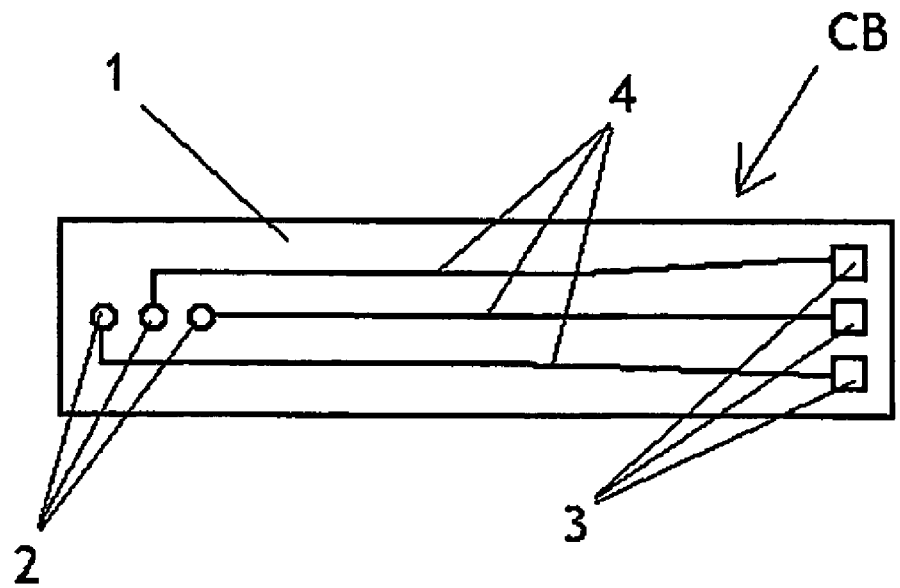
FIG. 1 is a top view showing a basic cell for an electrode carrier guide according to an embodiment of this invention.
Figure 2:
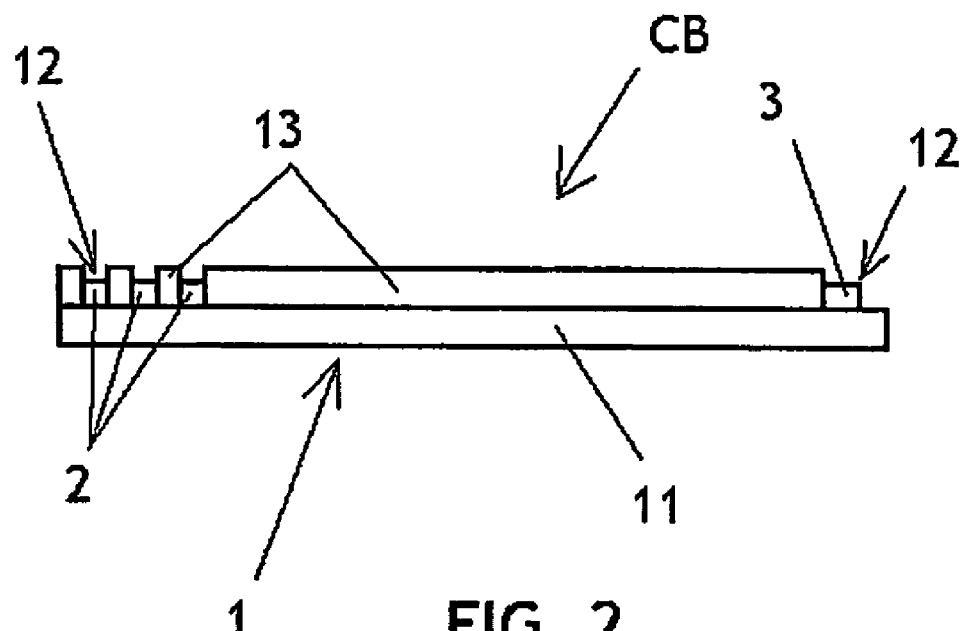
FIG. 2 is a front view of the cell from FIG. 1.

FIGS. 1 and 2 depict roughly an embodiment of basic cell CB. It must be highlighted that the following drawings are not in proportion to real cells and electrode carrier guides, in order to provide a clearer representation. In particular, the thicknesses have been greatly exaggerated compared to the rest of the measures, in order to show the structure of all the components.

A basic cell CB, in the illustrated embodiment, has a body 1 of electricity-insulating material, with an elongate and flat main structure, presenting three electrodes 2 on one end. Each electrode 2 is connected to a contact 3, placed on the other end of the cell, through a track 4.

Electrodes 2 and contacts 4, all of them made of a conductive material, are exposed to body 1 of the cell; that is, the insulating material of the body does not cover them.

On the following pages it will be precisely described the physical and geometrical characteristics of the basic cells and its production method.

Figure 3:
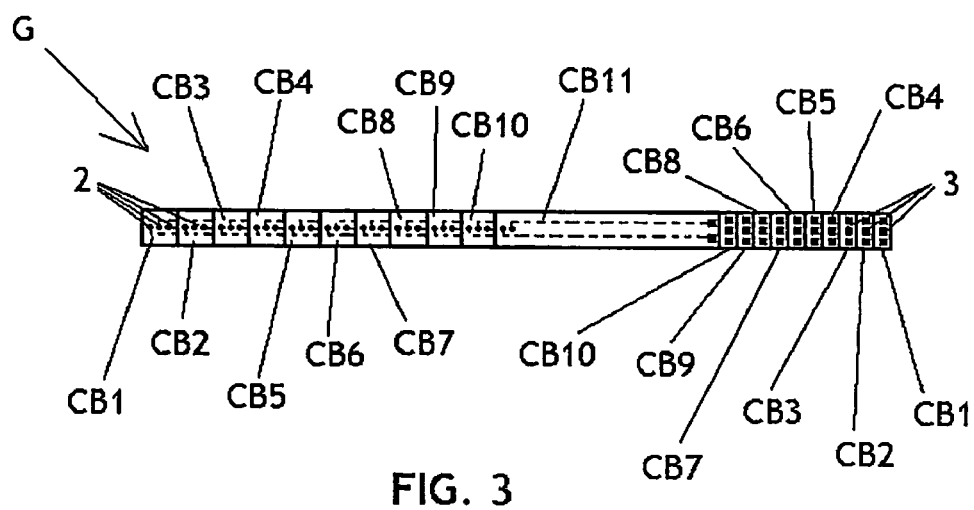
FIGS. 3 and 4 are, respectively, a top and a front view of an electrode carrier guide created by stacking a series of basic cells.
Figure 4:
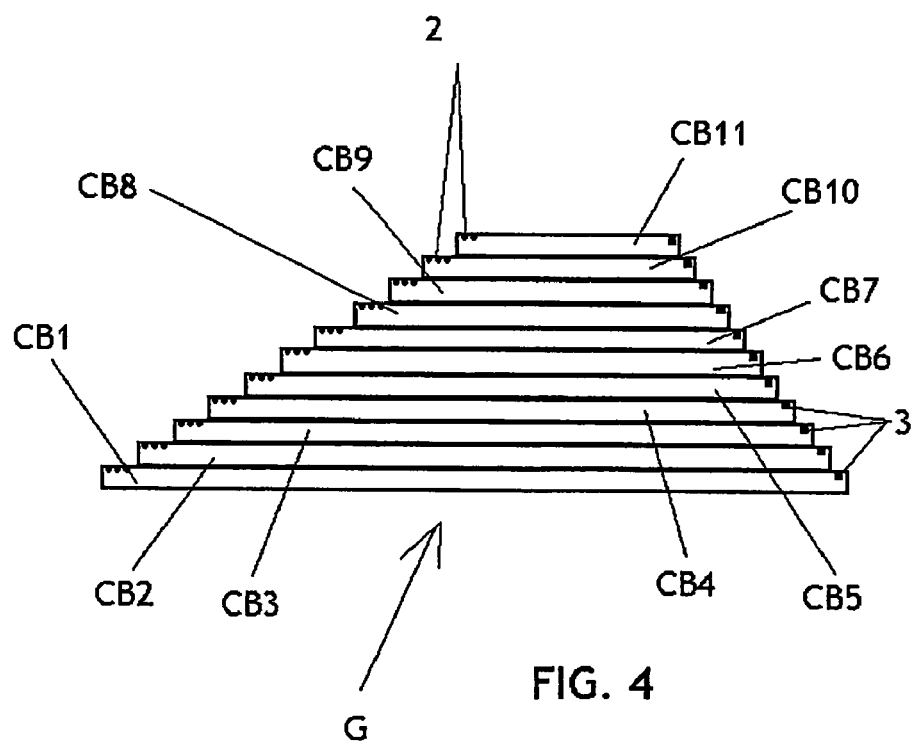
Figure 9:
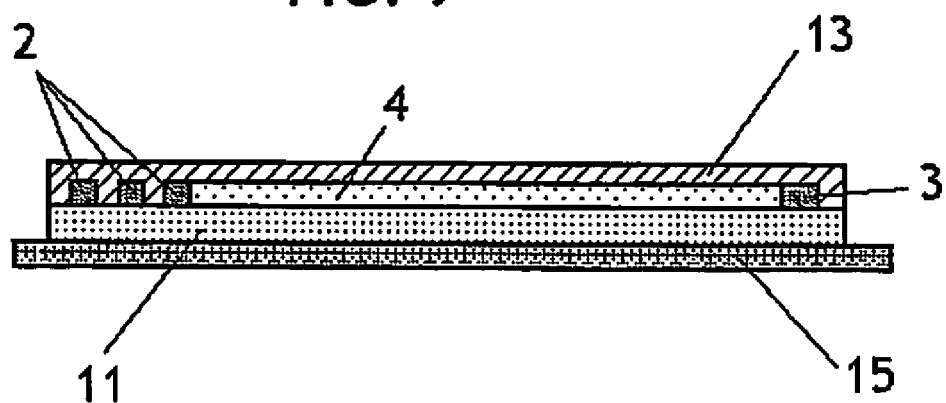

As shown on FIGS. 3 and 4, an electrode carrier guide G, according to an embodiment of this invention, is formed by the superposition of basic cells CB1, CB2, CB3 . . . CB11 similar to the one described, and each of them includes electrodes 2 and contacts 3. The superior cell CB11, given its length, only has two electrodes.

Each and every basic cell composing the carrier guide G has roughly the same width and thickness, but not the same length. They superpose in a pyramidal shape, so that electrodes 2 and contacts 3 of the basic cells are exposed, while tracks 4 between each electrode and its contact remain captured in the cells' material, the cells being isolated from each other.

Basic cells CB1 to CB11 have, in this example, lengths ranging from 45 mm to 12.5 mm approximately, and a width of some 2 mm. The length between electrodes is 0.75 µm approximately. The thickness of an isolated basic cell (FIG. 2) is 8 µm approximately. However, when superposing basic cells to create a carrier guide G, you are in fact placing each cell's electrodes and contacts directly on the body of the underlying cell in such a way that basic cells stacked to create carrier guide G are only 40 µm. thick. A further explanation on this will be given when describing the production method.

An electrode carrier guide G of 44 μm approximately is produced by superposing eleven basic cells as indicated in the carrier guide from FIGS. 3 and 4. This carrier guide, 25 mm long, presents 32 electrodes. Due to the size and the flexibility of the implantable system, the carrier guide is suitable for an implant that may be inserted between the spiral ligament and the endosteum, while presenting an elevated number of electrodes.

FIG. 5 shows another embodiment of a basic cell CB' according to the invention; cell CB' is similar to that in FIGS. 1 and 2, except in that the body 1' of the cell, in this case, is lancet-shaped. This shape is most suitable for the implantation in a patient's cochlea, since the width of the carrier guide may be reduced down to 0.5 mm in the area where it is going to be placed at the level of the cochlea's spiral ligament.

Before describing an example of the production method of an electrode carrier guide G, the structure and materials of a basic cell shall be explained, referring again to FIGS. 1 and 2.

Cell CB presents a base layer 11, made of a flexible, electricity-insulating material, in this case a polyimide (Pyralin®), though other materials may be used, such as silicone, PTFE (Teflon®), PET (Mylar®) and polymers based on paraxylene (Parylene®), and so on.

On base layer 11 you will find a metallization layer 12, which includes electrodes 2, tracks 4 and contacts 3. Some suitable materials for this layer are gold, platinum, or an alloy of platinum and, for example, 10% of iridium. This alloy is a better resistant to corrosion.

Between base layer 11 and metallization layer 12 stands a thin layer (not represented) made of titanium, tantalum, chrome or any other material that improves the adhesion of the metallization layer to the base layer.

Finally, on the metallization layer there is an insulating layer 13, made of the same material that base layer 11, which only leaves exposed electrodes 2 and contacts 3.

As it has been previously said, when producing carrier guide G the insulating layer 13 of the inferior basic cell is base layer 11 of the next cell, on which the metallization layer is placed.

Figure 10:
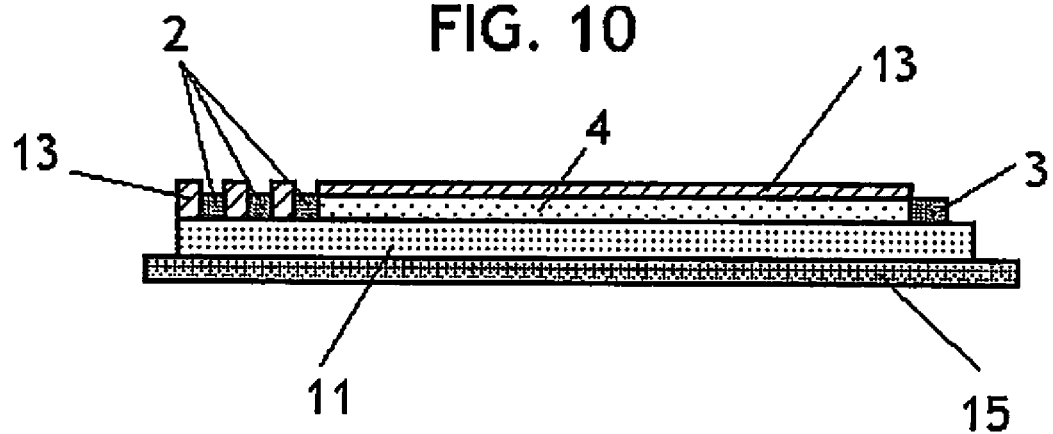

Now it will be briefly described a method for manufacturing a carrier guide G according to an embodiment of this invention (FIGS. 6 to 11).

a) First, prepare a sacrificial wafer of silicon 15 (FIG. 6), on which carrier guide G will be created. Preparation requires an ultrasonic bath of the wafer in trichloroethylene, acetone, alcohol and water during 5 minutes each, plus rinse off and dry off in spinner.

b) On the wafer 15, place a base layer 11 of 4 μm made of Pyralin® (FIG. 7) by spinner; then soft bake it during 30 minutes at 120° C. to provide it with better chemical properties and to partially polymerize it, and lastly hard-bake it at 300° C., to provide the material with the high chemical and mechanical resistance needed to be applied to implants.

c) During the next step, clean once again the wafer, place a photosensitive resin layer by spinner, soft-bake this resin (30 minutes at 90° C.), and use photolithography to define the geometry of the electrodes, tracks and contacts, and make a complete hard-bake of the resin at 110° during 35 minutes.

d) Sputter on the resin the thin layer of chrome to favor adhesion, and the platinum metallization layer 12, of 200 μm thick approx.; then, lift off and dilute in acetone at 45° C. and ultrasounds. The resin is eliminated, the chrome and the platinum outside the geometrical areas defined by lithophotography. Electrodes 2, contacts 3 and tracks 4 on base layer 11 are thus defined (FIG. 8).

e) Clean the wafer again, same procedure as in the first phase; and place once again the Pyralin by spinner, then soft-bake it during 30 minutes at 120°. Thus, an insulating layer 12 (FIG. 9) is created. It totally covers the metallization layer. This insulating layer is 4 μm thick.

f) Now you have to create the accesses for the electrodes and contacts through the material of the insulating layer 13, by drawing access windows with a photolithography technique and a chemical attack. The result is a complete basic cell on the wafer 15 (FIG. 10). You must now hard-bake it at 300° C.

Figure 11:
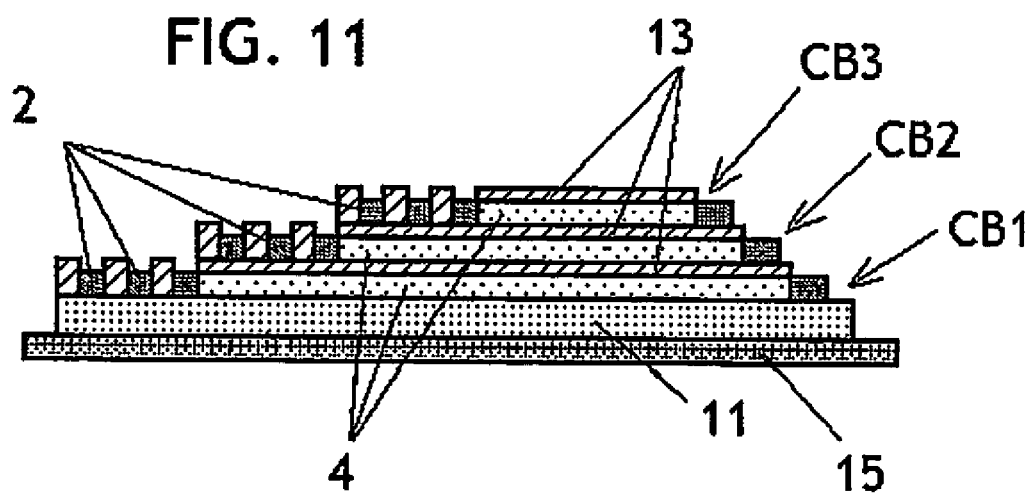

On the first basic cell, by successively repeating this process from step (c) onwards, you may create more stacked basic cells, till you complete the carrier guide on the wafer 15. On FIG. 11 is shown an example of a carrier guide comprising three cells.

You may create a plurality of electrode carrier guides simultaneously on one wafer 15, each carrier guide next to the other. In this case, once the carrier guide creation is over, each carrier guide may be obtained by cutting the wafer, for example, with an automated saw.

In case you are creating lancet-shaped cells and carrier guides, such as the one represented on FIG. 5, during step (f) of the process, access windows may be designed in such a way that all the extra Pyralin® is eliminated and the lancet-shape of the carrier guides is defined. The resulting carrier guides will be separated from each other on wafer 15. However, is the cells are rectangular-shaped, you must cut through the wafer to separate carrier guides.

In both cases, the last phase of the process is to eliminate the silicon wafer, by diluting it in $HF$—$HNO_3$ (1:1), to obtain the finished carrier guides.

The solicitants have pursued essays on basic cells and carrier guides obtained through the described processes, with both geometrical shapes (rectangular cells and lancet-shaped cells). These assays have confirmed the flexibility and electrical continuity between each electrode and its contact, the isolation between tracks and adherence between layers of the resulting product.

Rectangular geometry has resulted being more suitable to guarantee isolation between tracks.

Regarding isolation, there are several methods to form tracks. Tracks must have similar positions in each and every basic cell, so that tracks of adjacent cells are superposed on each other. On the other hand, you may create two different kinds of cells, placing the three tracks closer to each other and thus using just half the cell, and superposing alternate cells, so that the position of the tracks of a cell does not coincide with the position of the tracks of the adjacent cells. This solution improves isolation of the layers, but increases the risk of contact between the tracks of one cell.

No matter how specific the represented and described the embodiment of this invention is, the expert obviously may introduce changes or substitute some details by other technically equivalent, without diverging too much from the field of protection defined by the attached claims.

For example, the materials and number of electrodes in each basic cell, as well as the position of the tracks and the geometry of the cells may be different from those represented, according to the biomedical requirements and criteria of each case.

The invention claimed is:

1. An electrode carrier guide for a cochlear implant comprising:
    a plurality of electrodes, wherein each electrode is connected to a corresponding contact through a conducting track; and
    at least two overlapping basic cells, the basic cells comprising:

a base layer made of electrically insulating material; and
a layer of electrically conducting material arranged on the base layer;
wherein the electrode carrier guide is elongated and substantially flat, and wherein the electrodes, conducting tracks and contacts are formed from the electrically conducting material.

2. The electrode carrier guide of claim 1, wherein the two overlapping basic cells comprise an overlying and an underlying basic cell, and wherein the overlying basic cell has a length shorter than the length of the underlying basic cell and covers the underlying basic cell, except for an electrode region at one end of said underlying cell in which the electrodes are located, and a contact region at the opposite end of said underlying cell in which the contacts are located.

3. The electrode carrier guide of claim 2, wherein the basic cell comprises an insulating layer arranged on the electrically conducting layer, wherein the insulating layer comprises access openings in correspondence with each electrode and the corresponding contact.

4. The electrode carrier guide of claim 3, wherein the insulating layer of the underlying cell comprises the base layer of the overlying cell.

5. The electrode carrier guide of claim 2, wherein at least two cells comprise three electrodes essentially aligned in a longitudinal direction of the cells.

6. The electrode carrier guide of claim 2, wherein the width of the basic cells ranges from 0.3 mm to 2.5 mm.

7. The electrode carrier guide of claim 2, wherein the thickness of the base layer ranges from 2 .mu.m to 5 .mu.m. and the thickness of the electrically conductive layer ranges from 0.1 .mu.m to 0.5 .mu.m.

8. The electrode carrier guide of claim 2, wherein the distance between the electrodes of the basic cells range from 0.25 .mu.m to 10 .mu.m.

9. The electrode carrier guide of claim 2, wherein the basic cells narrow in the longitudinal portion where the electrodes are arranged.

10. The electrode carrier guide of claim 2, wherein the base layer material is selected from the group consisting of PTFE, PET, polyimide, silicone and paraxylene based polymers.

11. The electrode carrier guide of claim 2, wherein the electrically conducting layer is made of a material selected from the group consisting of gold, platinum and platinum-iridium alloy.

12. The electrode carrier guide of claim 2, wherein at least one basic cell comprises a film made of a material suitable for enhancing adherence, wherein the film is arranged between the base layer and the electrically conducting layer of said cell.

13. The electrode carrier guide of claim 12, wherein the film is selected from the group comprising titanium, tantalum and chrome.

14. A cochlear implant comprising the electrode carrier guide of claim 2.

15. A method for manufacturing an electrode carrier guide for a cochlear implant comprising:
a first step of forming a basic cell having the following sub-steps:
preparing a sacrificial wafer;
depositing a base layer made of an electrically insulating material on the wafer;
depositing a layer of photosensitive resin on the electrically insulating layer;
photolithographically designing a region comprising a geometry of electrodes, conducting tracks, and contacts;
depositing a layer made of an electrically conducting material onto the resin layer for forming the electrodes, conducting tracks, and contacts;
removing the resin and electrically conducting material deposited outside the photolithographically designed region;
depositing a second electrically insulating layer onto the electrically conducting layer, wherein the second electrically insulating layer completely covers the electrically conducting layer;
forming access windows in the second electrically insulating layer, wherein the access windows provide access to the underlying electrodes and contacts.
repeating the depositing a photosensitive resin sub-step to the forming access windows sub-step to form at least two basic cells; and
removing the sacrificial wafer;
wherein the electrode carrier guide is elongated and substantially flat, and further wherein each electrode is connected to a corresponding contact through a conducting track.

16. The method of claim 15, further comprising:
forming two overlapping basic cells comprising an overlying and an underlying basic cell, wherein the overlying basic cell has a length shorter than the length of the underlying basic cell and covers the underlying basic cell, except for an electrode region at one end of said underlying cell in which the electrodes are located, and a contact region at the opposite region at the opposite end of said underlying cell in which the contacts are located.

17. The method of claim 16, further comprising:
forming at least two electrode guides on the wafer.

18. The method of claim 17, further comprising:
separating the at least two electrode carrier guides by cutting the wafer.

19. The method of claim 16, further comprising:
curing at least one of the deposited layers.

20. The method of claim 16, further comprising:
depositing a film of material suitable for enhancing adherence, wherein the film is arranged between the base layer and the electrically conducting material of at least one cell.

* * * * *